US010092641B2

(12) United States Patent
Laulicht et al.

(10) Patent No.: US 10,092,641 B2
(45) Date of Patent: Oct. 9, 2018

(54) METHODS FOR EFFECTIVELY AND RAPIDLY DESENSITIZING ALLERGIC PATIENTS

(71) Applicant: Perosphere Inc., Danbury, CT (US)

(72) Inventors: Bryan E. Laulicht, Danbury, CT (US); Sasha H. Bakhru, Providence, RI (US); Solomon S. Steiner, Mount Kisco, NY (US); Edith Mathiowitz, Brookline, MA (US)

(73) Assignee: Perosphere Technologies Inc., Danbury, CT (US)

( * ) Notice: Subject to any disclaimer, the term of this patent is extended or adjusted under 35 U.S.C. 154(b) by 0 days.

(21) Appl. No.: 15/480,564

(22) Filed: Apr. 6, 2017

(65) Prior Publication Data

US 2017/0209567 A1   Jul. 27, 2017

Related U.S. Application Data

(63) Continuation of application No. 14/240,706, filed as application No. PCT/US2012/053145 on Aug. 30, 2012.

(60) Provisional application No. 61/529,479, filed on Aug. 31, 2011.

(51) Int. Cl.
*A61K 39/00* (2006.01)
*A61K 39/35* (2006.01)
*A61K 39/36* (2006.01)
*A61K 39/38* (2006.01)
*A61M 37/00* (2006.01)

(52) U.S. Cl.
CPC ......... *A61K 39/35* (2013.01); *A61M 37/0015* (2013.01); *A61K 2039/54* (2013.01); *A61K 2039/55511* (2013.01); *A61K 2039/55555* (2013.01); *A61K 2039/55583* (2013.01); *A61K 2039/577* (2013.01); *A61M 2037/003* (2013.01); *A61M 2037/0023* (2013.01); *A61M 2037/0061* (2013.01)

(58) Field of Classification Search
None
See application file for complete search history.

(56) References Cited

U.S. PATENT DOCUMENTS

| | | | | |
|---|---|---|---|---|
| 5,811,128 A * | 9/1998 | Tice | ..................... | A61K 9/1647 424/237.1 |
| 6,334,856 B1 | 1/2002 | Allen | | |
| 6,611,707 B1 | 8/2003 | Prausnitz | ............. | A61B 5/1411 604/21 |
| 7,473,247 B2 | 1/2009 | Mikszta | ................. | A61K 39/12 604/507 |
| 7,611,481 B2 | 11/2009 | Cleary | ................. | A61B 17/205 604/27 |
| 7,942,827 B2 | 5/2011 | Mir | ...................... | A61B 5/0059 600/556 |
| 8,182,805 B2 | 5/2012 | Viskari | | |
| 8,540,672 B2 | 9/2013 | McAllister | ........ | A61M 37/0015 604/136 |
| 2005/0095298 A1 | 5/2005 | Gronlund | ............... | A61K 39/35 424/489 |
| 2008/0269666 A1 * | 10/2008 | Wang | ................... | A61B 17/205 604/21 |
| 2009/0130127 A1 | 5/2009 | Tokumoto | | |
| 2009/0270347 A1 * | 10/2009 | Strong | ................. | A61K 9/0043 514/55 |
| 2010/0151000 A1 * | 6/2010 | Thomas | ................. | A61K 9/127 424/450 |
| 2010/0260821 A1 | 10/2010 | Dupont | | |

FOREIGN PATENT DOCUMENTS

| | | |
|---|---|---|
| GB | 1055465 | 1/1967 |
| WO | 0208429 | 4/2002 |
| WO | 2002067863 | 9/2002 |
| WO | 2004019978 | 3/2004 |
| WO | 2007059979 | 5/2007 |
| WO | 2008043157 | 4/2008 |
| WO | 2008130382 | 10/2008 |
| WO | 2008153541 | 12/2008 |
| WO | 2009083589 | 7/2009 |

(Continued)

OTHER PUBLICATIONS

Erdos, et al., "Dissolving microneedle arrays effectively deliver soluble and particulate biologically active molecules into the skin", J. Invest. Derma., 129:S117 Abstract 698 (2009).

Li, et al., "Chitosan microparticles loaded with mite group 2 allergen Der f 2 alleviate asthma in mice", J Invest. Allergol Clin Immunol., 18(6):454-69 (2008).

Scholl, et al., "Review of novel particulates antigen delivery systems with special focus on treatment of type I allergy", J Conttol Release, 104(1):1-27 (2005).

European Extended Search Report for EP 12828090 dated Jul. 14, 2015.

Jin, et al., "Mass producible and biocompatible microneedle patch and functional verification of its usefulness for transdermal drug delivery", Biomed Microdevices, 11(8):1195-1203 (2009).

(Continued)

Primary Examiner — Nora M Rooney
(74) Attorney, Agent, or Firm — Pabst Patent Group LLP

(57) ABSTRACT

Methods and compositions for delivering antigens to the lymphatic system in doses that desensitize patients to future exposure to antigens have been developed. Rapid desensitization is achieved by introducing small quantities of antigen into the lymphatic system. In preferred embodiments, the compositions are administered to yield therapeutically effective levels of antigen within the lymph, where macrophages reside in the greatest concentration, by intradermal administration, using for example, microneedles or micro articles, oral administration, using for example, enteric coated capsules or tablets, or autologous transfusion. In some embodiments, the methods and compositions for delivering antigens orally achieve uptake by the Peyer's patches of the small intestines.

8 Claims, 1 Drawing Sheet

(56) References Cited

FOREIGN PATENT DOCUMENTS

WO 2009141388 11/2009

OTHER PUBLICATIONS

Sachdeva and Baoga, "Microneedles and their applications", Recent Patents on Drug Delivery Formulation, 5:95-132 (2011).
Von Moos, et al., "Novel administration routes for allergen-specific immunotherapy: a review of intralymphatic and epicutaneous allergen-specific immunotherapy", Immunology Allergy Clinics of North America,31(2):391-408 (2011).
European Search Report for EP 12828090 dated Mar. 20, 2015.
Berger, "Th1 and Th2 responses: what are they?", BMJ, 321:424.1 (2000).
Gerada, et al., "Relation between house-dust endotoxin exposure, type 1 T-cell development, and allergen sensitisation in infants at high risk of asthma", Lancet, 355(9216):1680-3 (2000).
Wu, et al., "The Dermatophagoides pleronyssinus group 2 allergen contains a universally immunogenic T cell epitope", J Immunol., 169(5):2430-5 (2002).
Mitragotri et al. 'Overcoming the challenges in administering biopharmaceuticals: formulation and delivery strategies.' Nature Rev. 13:655-672, 2014.
Blumenthal et al. 'Definition of an allergen.' Allergens and Allergen Immunotherapy. Ed. R. Lockey et al. New York: Marcel Decker, 2004.37-50.
Secrist et al., J. Exp. Med. 176:2123, 1993.
Bjorksten et al. 'Clinical and immunological efects of oral immunotherapy with a standardized birch pollen extract.' Allergy, 41:290-295, 1986.
Bai, et al., Efficient induction of immune responses through intradermal vaccination with N-trimethyl chitosan containing antigen formulations, J Control Release, 142:374-383 (2010).
Japanese Office Action for corresponding JP application JP 2014-528602 dated Mar. 2, 2017.

* cited by examiner

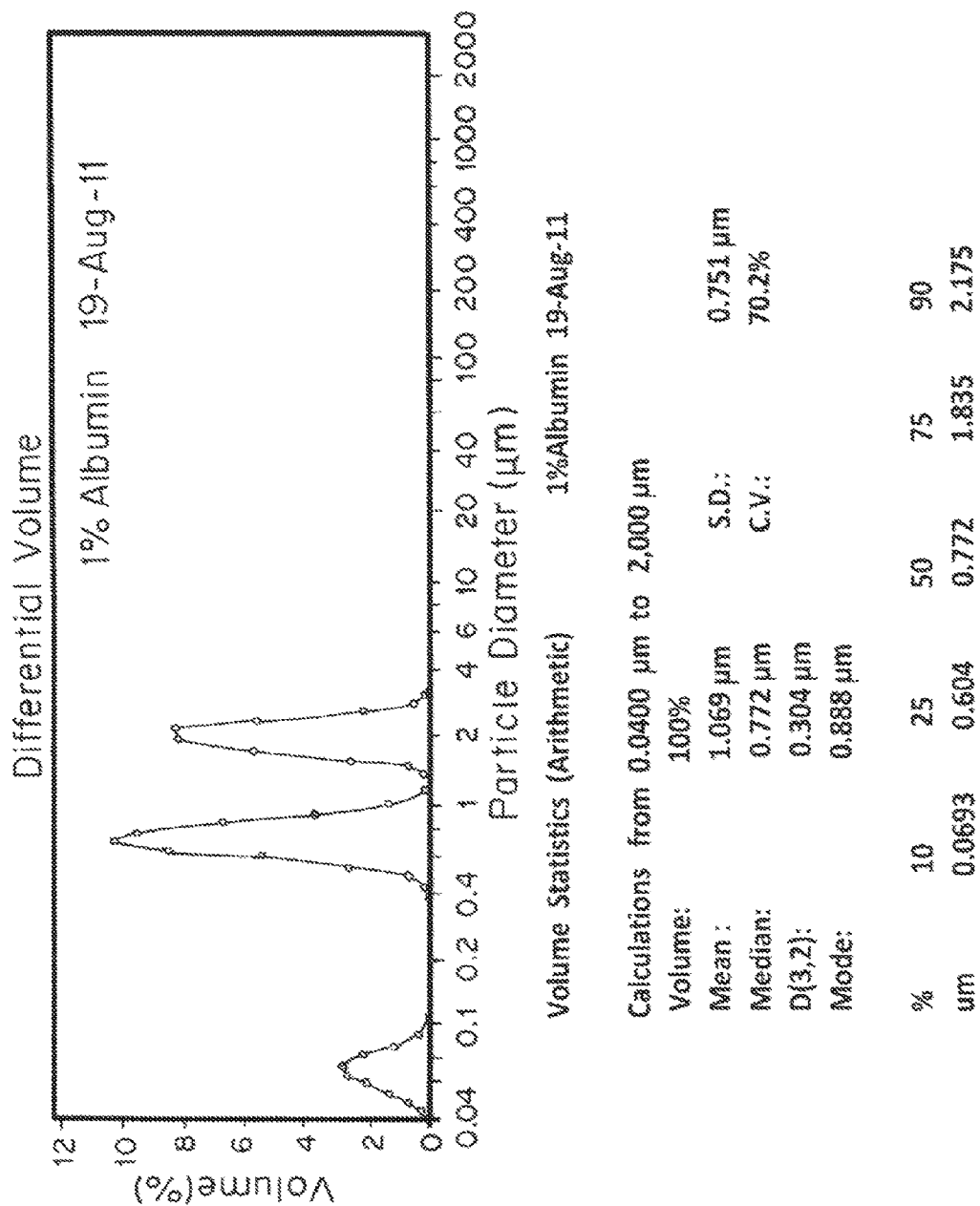

METHODS FOR EFFECTIVELY AND RAPIDLY DESENSITIZING ALLERGIC PATIENTS

CROSS-REFERENCE TO RELATED APPLICATION

This application is a continuation of U.S. application Ser. No. 14/240,706, filed Feb. 24, 2014, entitled "Methods for Effectively and Rapidly Desensitizing Allergic Patients", which is a § 371 application of the International Application No. PCT/US2012/053145, filed in the United States Receiving Office for the PCT on Aug. 30, 2012, which claims the benefit of and priority to U.S. Provisional Application No. 61/529,479 filed in the United States Patent and Trademark Office on Aug. 31, 2011, the disclosures of which are incorporated herein by reference.

FIELD OF THE INVENTION

The present invention is generally in the field of compositions to induce tolerance to allergens.

BACKGROUND OF THE INVENTION

Fifty-five percent of people in the United States test positive to one or more allergens. According to the Asthma and Allergy Foundation, allergies are the fifth most common cause of chronic disease in the United States and third in children. Approximately ten million Americans are allergic to cat dander. Approximately seven percent of allergy sufferers have skin allergies, six percent have dietary allergies, and four percent have insect allergies as of 2007.

Allergen immunotherapy, also known as allergy shots, is a form of long-term treatment that decreases symptoms for many people with allergic rhinitis, allergic asthma, conjunctivitis (eye allergy) or stinging insect allergy. Allergy shots decrease sensitivity to allergens and often lead to lasting relief of allergy symptoms even after treatment is stopped. This makes it a cost-effective, beneficial treatment approach for many people.

Allergy shots work like a vaccine. The body responds to injected amounts of a particular allergen, given in gradually increasing doses, by developing immunity or tolerance to the allergen by producing immunoglobulin G ("IgG") instead of IgE. Allergy shots are not used to treat food allergies. The best option for people with food allergies is to strictly avoid that food.

There are two phases:

Build-up phase. This involves receiving injections with increasing amounts of the allergens about one to two times per week. The length of this phase depends upon how often the injections are received, but generally ranges from three to six months.

Maintenance phase. This begins once the effective dose is reached. The effective maintenance dose depends on the level of allergen sensitivity and the response to the build-up phase. During the maintenance phase, there will be longer periods of time between treatments, ranging from two to four weeks. Symptoms may decrease during the build-up phase, but it may take as long as 12 months on the maintenance dose to notice an improvement. If allergy shots are successful, maintenance treatment is generally continued for three to five years. Allergy shots have shown to decrease symptoms of many allergies. It can prevent the development of new allergies, and in children it can prevent the progression of allergic disease from allergic rhinitis to asthma. The effectiveness of allergy shots appears to be related to the length of the treatment program as well as the dose of the allergen. Some people experience lasting relief from allergy symptoms, while others may relapse after discontinuing allergy shots.

Allergy is regarded as a Th2 weighted imbalance, and cytokines produced by Th2 lymphocytes, including interleukins 4, 5, and 13, have been associated with the promotion of IgE and eosinophilic responses in atopy. Berger, *BMJ*, 321:424.1 (2000). Ways to redirect allergic Th2 responses in favor of Th1 responses should be beneficial in reducing incidences of allergic reactions.

In summary, better, and less invasive, means for inducing tolerance to allergens is needed. Rapid, effective desensitization to allergens is a significant unmet medical need that would alleviate a tremendous burden of chronic patient suffering.

It is therefore an object of the present invention to provide methods and compositions to induce tolerance to allergens.

SUMMARY OF THE INVENTION

Methods and compositions for delivering antigens to the lymphatic system in doses that desensitize patients to future exposure to antigens have been developed. Rapid desensitization is achieved by introducing small quantities of antigen into the lymphatic system. In preferred embodiments, the compositions provide therapeutically effective levels of antigen within the lymph, where macrophages reside in the greatest concentration. The compositions can be administered by intradermally, for example, via microneedles or microparticles, orally, for example, via enteric coated capsules or tablets, or by autologous transfusion.

In some embodiments, the methods and compositions for delivering antigens orally achieve uptake by the Peyer's patches of the small intestine. In some embodiments, a population of macrophages exposed to antigen is isolated in whole or fractionated blood for autologous transfusion into the patient.

In some embodiments compositions preferably increase immunoglobulin G levels specific to the allergen without significantly increasing the immunoglobulin E levels specific to the allergen. In other embodiments, the compositions improve allergic desensitization as measured by decreased Th2 response (for example, Th2-type cytokines) and/or increase Th1 responses, for example, Th1-type cytokines.

BRIEF DESCRIPTION OF THE DRAWINGS

FIG. 1 shows Coulter particle sizing data of ovalbumin-chitosan microparticles for allergen desensitization.

DETAILED DESCRIPTION OF THE INVENTION

I. Definitions

As used herein, "rapid desensitization" refers to increasing the tolerance to one or a group of allergens more quickly than in the absence of treatment.

As used herein, the term "tolerance" refers to the level of allergic response to a particular quantity of allergen.

As used herein, the term "antigen" refers to a substance or substances alone or in combination that when introduced into the lymphatic system induces production of antibodies that bind to a fraction of the molecule or molecules.

As used herein, the term "allergen" refers to a substance that could cause an allergic reaction in a patient.

As used herein, the term "allergic reaction" refers to any untoward response to an allergen.

As used herein, "lymphatic system" refers to the network of lymph containing vessels.

As used herein, the term "intradermal" refers to residing within the dermal layer of skin or between the epidermal and dermal layers.

As used herein, the term "microneedle" refers to a protrusion capable of penetrating the human epidermis in which its largest axis is less than three millimeters in length.

As used herein, "sharp microneedle" refers to any microneedle that is capable of penetrating the human epidermis.

As used herein, the term "microparticle" refers to any shaped particle that has at least one dimension less than one millimeter in size.

As used herein, "autologous transfusion" refers to a whole or fractionated blood sample returned to the patient from whom it was taken by injection or intravenous infusion.

As used herein, "equivalent circle diameter" refers to the diameter of a circle having the same cross-sectional area as the object being measured.

As used herein, "reservoir-type delivery system" refers to formulations containing one or multiple antigen-rich and antigen-poor regions within each discrete element of the delivery system.

As used herein, "matrix-type delivery system" refers to formulations containing a random distribution of antigen within each discrete element of the delivery system.

As used herein, the term "biodegradable" refers to a class of materials that undergo reductions in molecular weight upon introduction into a cell-containing environment.

As used herein, the term "bioadhesive" refers to a class of materials that adheres to one or more biological substrates.

As used herein, the term "adjuvant" refers to any agent that increases the immunological response to an antigen.

As used herein, the term "tip radius" refers to the radius of a circle equivalent in cross-sectional area to the smallest aspect of a microstructure.

As used herein, the term "micropillar" refers to any microstructure that is longer than it is wide and mechanically supports another microstructure.

As used herein, "enteric coating" refers to any material that can protect an antigen from acidic degradation within the human stomach for a sufficiently long period of time such that at least ten percent of the antigen is delivered on average into the small intestines in an active form. As used herein, "enteric protective polymer" refers to any polymer that protects an antigen from acidic degradation within the human stomach for a sufficiently long period of time such that at least ten percent of the antigen is delivered on average into the small intestines in an active form.

As used herein, the term "encapsulant" refers to any material that encapsulates another substance.

As used herein, "water soluble polymer" refers to a class of polymers for which more than ten percent of the mass of the polymer enters solution in a volume of water or aqueous fluid.

As used herein, "pH sensitive polymer" refers to a class of polymers that exhibit a pH dependent solubility profile.

As used herein, "enzymatically degradable polymer" refers to a class of polymers containing regions that are chemically altered in the presence of one or more enzymes.

As used herein, "enzyme cleavable polymer" refers to a class of polymers enzymatically degraded to yield a decrease in molecular weight.

As used herein, the term "peptide" refers to at least two of any amino acid or amino acid derivative linked by a peptide bond.

As used herein, the term "phlebotomy" refers to any means of obtaining a blood sample from a patient.

As used herein, the term "net charge altering agent" refers to any compound that alters the net charge of a solution or suspension temporarily or permanently.

II. Compositions

A. Allergens

Clinically available allergens for inducing tolerance can be utilized. Examples include peanut allergens, including, but not limited to peanut flour, *Arachis hypogaea* 1 (Ara h 1), *Arachis hypogaea* 1 (Ara h2); cat allergens, including but not limited to, *Felis domesticus* allergen 1-4 (Fel D1, Fel D2, Fel D3, Fel D4), and cat IgA; house dust mite allergens, including, but not limited to, *Dermatophagoides pteronyssinus* group 1 and 2 allergens (DER p1 and DER p2); other house dust allergens, for example, house dust endotoxin; pollen allergies, including, but not limited to Bet v and Bet v2; bee sting allergens, for example, phospholipase A2 (PLA2) one of the major bee venom allergen, wasp allergens; cockroach calyx, penicillin, sulfonamides, salicylates, albumen, pollen, or their derivatives. U.S. Pat. No. 8,182,805 to Viskari, et al. discloses enteroviruses useful for decreasing allergic sensitization, identified by their effect on regulatory T-cells and/or Th1/Th2-balance and/or production of immunoregulatory cytokines such as IL-10.

B. Formulations

In certain embodiments, the antigen is delivered in solution. In other embodiments, the antigen is delivered in suspension.

Microparticles

In those embodiments in which the antigen is delivered in suspension, the antigen is formulated such that at least seventy percent of the population of microparticles, more preferably at least eighty percent of the population, and most preferably at lest ninety percent of the population of microspheres is small enough to phagocytosed by macrophages or dendritic cells, and too large to be endocytosed in quantities sufficient to cause an untoward allergic response by other cell types. In specific embodiments, the microparticles of antigen are in an appropriate size range for macrophage engulfment, i.e., the microparticles have a mean equivalent circle diameter of between one and ten, more preferably between two and nine, and most preferably between three and six microns.

In certain embodiments, the mean diameter of the population of microparticles, in the case of irregularly shaped microparticles diameter refers to the diameter of a circle of equivalent cross-sectional area, is between two and nine microns, more preferably between three and eight microns, and most preferably between three and six microns. In certain embodiments, the at least seventy percent of, more preferably eighty percent of, and most preferably ninety percent of the diameter, or equivalent circle diameter, distribution within the population of administered antigen microspheres is within the range of one to ten microns, more preferably two to nine microns, and most preferably three to six microns.

In some embodiments, microparticles of antigen encapsulated in a polymer are administered orally as a reservoir-type or matrix-type delivery system. The microparticles are fabricated by one or a combination of the following techniques including, but not limited to, emulsion solvent evaporation, double emulsion solvent evaporation, ionic gelation, coacervation, membrane emulsification, supercritical fluid microencapsulation, spray drying, and hot melt microencapsulation.

In some embodiments the antigen is microencapsulated within a water-soluble polymer, or combination thereof, for example, polyvinyl alcohol, methylcellulose, hydroxypropyl methylcellulose, starch, dextran, albumin, and sodium alginate. In some embodiments, the antigen is microencapsulated in a pH-sensitive polymer that is stored at one pH and dissolves after entering the intradermal environment such as any of the following, or combination thereof, such as a polymer blend of acrylic acid and methacrylic acid, modified collagen, and modified crosslinked and un-crosslinked polyacrylic acids. In some embodiments, the antigen is encapsulated in a biodegradable polymer, or combination thereof, such as a polyhydroxyacid like polylactic acid, polyglycolic acid, or polylactic-co-glycolic acid, polyanhydride, polyorthoester, polyphosphate ester, polycaprolactone, and polyglycerol sebacate. In some embodiments, the antigen is encapsulated in a bioadhesive polymer, or combination thereof, such as polyfumaric-co-sebacic anhydride, chitosan, polyethylene maleic anhydride, catechol functional polymer, and lectin. In some embodiments, the antigen is encapsulated in an enzymatically cleavable polymer that is sensitive to degradation by macrophage lysozomal enzymes. In some embodiments, the enzymatically cleavable polymer contains peptide sequences cleaved by enzymes found in lysozomes, such as acid hydrolases and serine proteases. In some embodiments, the antigen is encapsulated in hydrogel polymers such as calcium alginate, chitosan and chitosan derivative complexes (e.g. alginate-chitosan), polyethylene glycol, and poly-2-hydroxyethyl methacrylate. In some embodiments, the antigen is microencapsulated in polyamino acids or combinations thereof such as polylysine, polyarginine, polyaspartate, and polyglutamate.

In some embodiments, the polymer microparticles containing antigen are administered within an enterically coated capsule or tablet. In some embodiments, the polymer encapsulant is an enteric protective polymer such as one or a combination of the following including, but not limited to, Eudragit®L100, Eudragit® L100-55, Eudragit 8100, and modified collagen. In some embodiments, the antigen is microencapsulated within a water-soluble polymer. In some embodiments, the antigen is microencapsulated a pH-sensitive polymer that is stored at one pH and dissolves after entering the intradermal environment such as any combination of the following including, but not limited to polymer blends of acrylic acid and methacrylic acid, modified collagen, and modified crosslinked and un-crosslinked polyacrylic acids. In some embodiments, the antigen is encapsulated in a biodegradable polymer such as any combination of the following including, but not limited to, polylactic acid, polyglycolic acid, polylactic-co-glycolic acid, polyanhydrides, polyorthoesters, polyphosphate esters, polycaprolactone, and polyglycerol sebacate. In some embodiments, the antigen is encapsulated in a bioadhesive polymer such as any combination of the following including, but not limited to polyfumaric-co-sebacic anhydride, chitosan, polyethylene maleic anhydride, catechol functional polymers, and lectins. In some embodiments, the antigen is encapsulated in an enzymatically cleavable polymer that is sensitive to degradation by macrophage lysozomal enzymes. In some embodiments, the enzymatically cleavable polymer contains peptide sequences cleaved by enzymes found in lysozomes, such as any combination of the following including, but not limited to acid hydrolases and serine proteases.

In some embodiments, release of the antigen from microcapsules can be accomplished using an encapsulating material that is specifically degraded by an enzyme or group of enzymes present within the phagocytic vesicles of a macrophage (e.g. phagosomes and phagolysosomes). In some embodiments, the antigen containing microparticles exhibit degradation kinetics tailored to release antigen once the macrophages leave the systemic circulation on average and return to the lymph after injection, in some embodiments microparticles release less than twenty five percent of the antigen within two days after injection, more preferably less than fifteen percent of the antigen within two days after injection, and most preferably less than ten percent of the antigen within two days after injection.

In a specific embodiment, the encapsulating material can contain chitosan or a chitosan derivative (e.g. alginate-chitosan). Chitosan and chitosan-derivatives are substrates for degradation by lysozyme within the macrophage cell body. Lysozyme is present in highest concentrations within the phagolysosome, where the antigen would be released from microcapsules over time by degradation of the beta 1,4-beta-linkages along the backbone of the chitosan or chitosan-derivative polysaccharide after phagocytosis of microcapsules. These macrophages subsequently release some of the free antigen within the lymph.

Hydrogels

In some embodiments, the antigen is encapsulated in hydrogel polymers such as any combination of the following including, but not limited to, calcium alginate, polyethylene glycol, and poly-2-hydroxyethyl methacrylate. In some embodiments, the antigen is microencapsulated in polyamino acids. In some embodiments, the antigen is encapsulated within more than one of the above polymers from a single or multiple groupings either physically mixed throughout each microparticle, or forming a core-shell morphology. In some embodiments the antigen is delivered along with an adjuvant excipients. In some embodiments, the adjuvant is a net charge altering agent such as, but not limited to one or a combination of charged amino acids including lysine, arginine, histidine, glutamate, and aspartate.

C. Adjuvants

Uptake by macrophages can be encouraged by decorating the surface of the microcapsules with "scavenger receptors", including, but not limited to, SR-AI and SR-AII or CD36, involved in triggering phagocytosis of apoptotic cells. In another embodiment, functionalizing the microcapsule surface with an antibody, antibody derivative, antibody fragment, or aptamer to a macrophage surface protein, e.g. F4/80, Macrosialin (FA-11), Sialoadhesin (SER-4, 3D6), Mannose receptors, or Dectin-1, can be used to enhance phagocytotic uptake of microcapsules.

In some embodiments the antigen is delivered along with an adjuvant. Adjuvants include, but are not limited to, highly charged polymers such as chitosan and polylysine.

In some embodiments, a net charge altering agent is incorporated into the allergen suspension or solution such as, but not limited to one or a combination of, charged amino acids including lysine, arginine, histidine, glutamate, and aspartate, to encourage macrophage engulfment.

III. Methods of Administration and Devices for Use Thereof

A. Individuals to be Treated and Treatment Regime

Patients to be Treated

Individuals to be treated include any patient who suffers from sensitivity to an allergen. In specific embodiments patients may suffer from any or a combination of food allergies, environmental allergies, dust mite allergy, insect bite or sting allergies, and pet allergies.

Therapeutic Regimen

Any one or a combination of the above treatment modalities are administered to a patient once a month for three months, more preferably twice a month for three to six months, and most preferably every fourteen days for a period of forty-two days. In some embodiments, the therapeutic regimen increases the immunoglobulin G levels within the patient, without significantly increasing the immunoglobulin E levels to induce allergen tolerance. In other embodiments, the compositions improve allergic desensitization as measured by decreased Th2 response (for example, Th2-type cytokines) and/or increase Th1 responses, for example, Th1-type cytokines. For example, the therapeutic regimen can reduce Th2 and/or increase Th1 responses. In these embodiments, the treatment regimen increases Th1-response, for example, by increasing interferon gamma and/or interleukin 10 and/or 12 production. Gerada, et al., *Lancet,* 13:355(9216):1680-3 (2000). The treatment regimen can reduce Th2-type cytokines, for example interleukins 4, 5, and 13, which have been associated with the promotion of IgE and eosinophilic responses in atopy. Berger, *BMJ,* 321:424.1 (2000).

B. Routes of Administration

Pharmaceutically acceptable excipients are utilized as appropriate for the specific route of administration. For example, for injection, the formulation can be prepared in sterile saline, water or phosphate buffered saline. Alternatively, hydrogels or dry particles may be injected, implanted or inserted with microneedles.

Intradermal Delivery using Microneedles

In a preferred embodiment, antigen is delivered by high-pressure intradermal injection through hollow microneedles. The high pressure is necessary to create a pocket in the dermis. High-pressure intradermal drug delivery is known in the art and described for example, in Gupta, et al., *Biomaterials,* 32:6823-6831 (2011) and U.S. Publication No. 20090157041, the contents of which are hereby incorporated by reference. In some embodiments, one or a plurality of solid microneedles is used to deliver the antigen intradermally. In these embodiments, the antigen is formulated as a matrix-type or reservoir-type delivery system within a biodegradable polymer microstructure capable of penetrating the epidermis when supported by a biodegradable or non-degradable backing support layer. To achieve epidermal penetration at minimal force, the tip radius of the microstructure is less than or approximately equal to twenty-five, more preferably ten, and most preferably five microns.

In these embodiments, the antigen is formulated as a matrix-type or reservoir-type delivery system within a biodegradable polymer microstructure capable of penetrating the epidermis when supported by a biodegradable or non-degradable backing support layer. To achieve epidermal penetration at minimal force, the tip radius of the microstructure is less than or approximately equal to twenty-five, more preferably ten, and most preferably five microns.

In specific embodiments, one or a combination of the following techniques such as micromolding, wet etching, dry etching, and laser cutting is used to fabricate the antigen into a biodegradable or water-soluble polymer in a sharp microstructure. The sharp biodegradable polymer microstructures are supported either by the same or a similar material, or a non-degradable support such as an array of metallic micropillar supports. When the device is placed into the skin, it penetrates the epidermis and contacts or enters the dermis. Each individual microneedle is approximately two and one half, more preferably less than one and one half, and most preferably less than one millimeter in length. In certain embodiments, a portion of or the entire biodegradable or water-soluble component of the microneedle array containing the antigen remains within the dermis after removal of the backing.

To encourage phagocytosis by macrophages and dendritic cells, the biodegradable or water-soluble portions remaining in the dermis have an equivalent circle mean diameter of between one and ten, more preferably between two and nine, and most preferably between three and six microns.

In specific embodiments, one or a combination of the following techniques such as micromolding, wet etching, dry etching, and laser cutting is used to fabricate the antigen into a biodegradable or water-soluble polymer in a sharp microstructure. The sharp biodegradable polymer microstructures are supported either by the same or a similar material, or a non-degradable support such as an array of metallic micropillar supports. When the device is placed into the skin, it penetrates the epidermis and contacts or enters the dermis. Each individual microneedle is approximately two and one half, more preferably less than one and one half, and most preferably less than one millimeter in length. In certain embodiments, a portion of or the entire biodegradable or water-soluble component of the microneedle array containing the antigen remains within the dermis after removal of the backing.

To encourage phagocytosis by macrophages and dendritic cells, the biodegradable or water-soluble portions remaining in the dermis have an equivalent circle mean diameter of between one and ten, more preferably between two and nine, and most preferably between three and six microns. In some embodiments, a net charge altering agent is incorporated into the allergen suspension or solution such as, but not limited to, one or a combination of charged amino acids, including lysine, arginine, histidine, glutamate, and aspartate, to encourage macrophage engulfment.

Oral Delivery

In some embodiments, microparticles of antigen are delivered orally in an enterically coated capsule or tablet.

Autologous Infusion Therapy

In some embodiments, microparticles of antigen or polymer-encapsulated antigen are delivered to macrophages recruited from blood of the patient and then returned to the patient by injection or infusion. Whole blood is obtained from the patient by phlebotomy. In some embodiments, the macrophages are separated from the whole blood by plating on tissue culture polystyrene or another material to which macrophages adhere. Microparticles of antigen or polymer-encapsulated antigen are introduced in suspension to the macrophages in an appropriate size range for phagocytosis. After a period of time sufficient for the macrophages to engulf a therapeutic quantity as part of an allergic desensitization regimen, the autologous macrophages are re-introduced into the patient by injection or intravenous infusion.

A proposed mechanism is that macrophages, dendritic cells in the skin, and Peyer's patches in the ileum will transport the particles into the lymph, where the T and B cells can begin antibody production.

A kit for this purpose could include heparinized vacuum collection tubes containing antigen encapsulated in particulate form, a heat block for incubation at physiological temperature (e.g. 37° C.), a syringe-coupled filter to separate the small, freely suspended microcapsules remaining after incubation from the blood, and a resuspension buffer for injection of the cells back into the patient. In one embodiment, the heating element is a Peltier heating and cooling device; in another, the heating element is a resistive heater. In one embodiment, the separation of macrophages from freely suspended antigen microparticles occurs by size exclusion. In another embodiment, the separation of macrophages from freely suspended antigen microparticles occurs based on differences in density between the microparticles and the macrophages.

The present invention will be further understood by the following non-limiting examples.

Example 1: Chitosan Microparticles for Antigen Delivery

Low molecular weight chitosan greater than 75 percent deacetylated was dissolved in 1 percent aqueous glacial acetic acid to create a 5 milligram per milliliter aqueous chitosan solution. 9 milliliters of aqueous 1% ovalbumin, 0.1% sodium tripolyphosphate were added drop-wise into 18 milliliters of the 5 milligram per milliliter aqueous chitosan solution while vortexing.

The resultant microparticles were sized by Coulter particle size analysis as shown in FIG. 1. To isolate the population of microparticles that are approximately 2 microns in apparent diameter, the resultant population is filtered through a 1 micron filter to produce microparticles suitable for allergic desensitization to ovalbumin.

Modifications and variations of the present invention will be obvious from the foregoing description and are intended to come within the scope of the following claims.

We claim:

1. A method for selective delivery to the lymphatic system comprising administering by intradermal injection of microparticles comprising one or more antigens through a hollow microneedles, the microparticles having a mean equivalent circle diameter in the range of one to ten microns and comprising chitosan or a chitosan derivative, that is an enzymatically cleavable polymer that is sensitive to degradation by macrophage lysozomal enzymes, the microparticles to be delivered to the cells in the lymph system, wherein less than twenty-five percent of the one or more antigens is released within forty eight hours after administration prior to uptake by macrophages, wherein the microparticles further comprise a net charge altering agent to promote macrophage engulfment and wherein the net charge altering agent is one or a combination of charged amino acids.

2. The method of claim 1 wherein the antigen is, one or a combination of peanut flour allergen, *Arachis hypogaea* 1 (Ara h1), *Arachis hypogaea* 2 (Ara h2), Fel D1, Fel D2, Fel D3, Fel D4, DER p1, DER p2, Bet v1, Bet v2, PLA2, bee sting allergen, wasp allergen, cockroach calyx allergen, penicillin allergen, sulfonamides, pollen allergen or house dust allergen.

3. The method of claim 1, wherein the microparticles are administered in a suspension.

4. The method of claim 1 wherein at least seventy percent of the microparticles are between three and six microns in equivalent circle diameter.

5. The method of claim 1 comprising delivering the microparticles through the hollow microneedles by application of high pressure.

6. The method of claim 1 wherein the microparticles release less than ten percent of the one or more antigens, within forty eight hours prior to uptake by macrophages.

7. The method of claim 1 wherein the microparticles are comprised of chitosan crosslinked with sodium tripolyphosphate.

8. The method of claim 1, comprising administering the microparticles for a period selected from the group consisting of once every fourteen days for a period of between 42 and 168 days, and once monthly for a period of between three and twelve months.

* * * * *